(12) United States Patent
Prien et al.

(10) Patent No.: US 6,864,046 B1
(45) Date of Patent: Mar. 8, 2005

(54) METHOD FOR COLLECTING AND PRESERVING SEMEN

(75) Inventors: Samuel D. Prien, Shallowater, TX (US); Dustie L. Johnson, Midland, TX (US)

(73) Assignee: Texas Tech University, Lubbock, TX (US)

(*) Notice: Subject to any disclaimer, the term of this patent is extended or adjusted under 35 U.S.C. 154(b) by 0 days.

(21) Appl. No.: 09/795,970

(22) Filed: Mar. 1, 2001

Related U.S. Application Data
(60) Provisional application No. 60/186,230, filed on Mar. 1, 2000.

(51) Int. Cl.$^7$ ............................ A01N 1/02; A61K 35/52
(52) U.S. Cl. ............................ 435/2; 435/374; 424/561
(58) Field of Search ................... 435/2, 374; 424/561, 424/94.1

(56) References Cited

U.S. PATENT DOCUMENTS

| | | | |
|---|---|---|---|
| 3,472,735 A | | 10/1969 | Yoshimasa |
| 3,973,003 A | | 8/1976 | Colas |
| 4,007,087 A | | 2/1977 | Ericsson |
| 4,329,337 A | * | 5/1982 | Sexton |
| 4,965,186 A | | 10/1990 | Grischenko |
| 5,494,800 A | * | 2/1996 | Smith, III |
| 5,495,719 A | * | 3/1996 | Gray, Jr. |
| 5,849,473 A | | 12/1998 | Cabrera |
| 5,863,715 A | | 1/1999 | Rajotte |
| 5,961,503 A | * | 10/1999 | Simmet et al. |
| 5,983,661 A | * | 11/1999 | Wiesman |

OTHER PUBLICATIONS

Bearden, J.H.; Fuquay, J.W., "Applied Animal Reproduction," Applied Animal Reproduction, 5th ed., Prentice–Hall (Upper Saddle River, New Jersey), p. 183–186.

Brinsko, S.P.; Varner, D.D., "Artifical Insemination and Preservation of Semen," Stallion Management, Veterinary Clinics of North America: Equine Practice, vol. 8 (No. 1), p. 205–218, (Apr. 1, 1992).

Grootegoed, J.A.; Den Boer, P.J., "Energy Metabolism of Spermatids: A Review," Cellular and Molecular Events in Spermiogenesis, Cambridge University Press (Cambridge, UK), p. 193–217, (Jun. 1, 1987).

Prins, G.S.; Weidel, L., "A Comparative Study of Buffer Systems and Cryoprotectants for Human Spermatozoa," Fertility and Sterility, The American Fertility Society (USA), vol. 46 (No. 1), p. 147–149, (Jul. 1, 1986).

Prien, S.D., "A Comparative Study of Calcium Utilization in Human and Porcine Spermatozoa," Animal Science, p. 28–150, (Aug. 1, 1991).

Keel, B.A.; Webster, B.W., "Laboratory Diagnosis and Treatment of Fertility," CRC Handbook, CRC Press (USA), p. 197–199.

Tao, J.; Du, J.; Kleinhans, F.W.; Critser, E.S.; Mazur, P.C.; Critser, J.K., "The Effect of Collection Temperature, Cooling Rate and Warming Rate on Chilling Injury and Cryopreservation of Mouse Spermatozoa," Journals of Reproduction & Fertility, p. 231–236, (Jun. 1, 1995).

Wright, P.J.; Parry, B.W., "Cytology of the Canine Reproductive System," Clinical Pathology: Part II, Veterinary Clinics of North America: Small Animal Practice, vol. 19 (No. 5), p. 851–874, (Sep. 1, 1989).

Seager, S.W.J.; Platz, C.C., "Collection and Evaluation of Canine Semen," Symposium on Reproductive Problems, Veterinary Clinics of America, vol. 7 (No. 4), p. 765–773, (Nov. 1, 1977).

Sherman, J.K., "Cryopreservation of Human Semen," Techniques of Human Andrology, Elsevier/North Holland Biomedical Press, p. 400–420, (Jun. 1, 1977).

* cited by examiner

*Primary Examiner*—Leon B. Lankford, Jr.
*Assistant Examiner*—Ruth A. Davis
(74) *Attorney, Agent, or Firm*—Jones, Tullar & Cooper PC

(57) ABSTRACT

A method for collecting and preserving semen of various animals including humans, canines, porcines, bovines, ovines and others involves collecting the semen into a collection vessel where the collection vessel is provided with an extender solution for the semen prior to its collection. Moreover, the extended is preferably maintained at a temperature close to normal body temperature of the species being collected over the time period of its collection. The extender is chosen to buffer the pH of the semen sample and to be isotonic with the semen. The volume of the extender in the collection vessel is preferably chosen such that the semen volume is initially diluted with twice its volume extender solution and some period thereafter the extended semen sample is diluted again at the same ratio. Collection into warmed extender media lessened the cold and pH shock to the spermatozoa, as shown by improved semen parameters. The extender solution is preferably rich in calcium ion. A collection vessel resembling an inverted Y is used for collecting distinct semen samples for comparative study.

12 Claims, 12 Drawing Sheets

Treatment by Time versus Control by Time-All Animals

Treatment by Time versus Control by Time-"Tolerant" Animals

Treatment by Time versus Control by Time-"Intolerant" Animals

Treatment
Time to Zero Percent Motility-"Tolerant" Animals

Treatment
Time to Zero Percent Motility-"Intolerant" Animals

Time to Last Full Insemination-Animals Within the 95% CI

Forward Progression- Treatment by Time versus Control by Time

METHOD FOR COLLECTING AND PRESERVING SEMEN

CROSS REFERENCE TO RELATED APPLICATIONS

This application claims the benefit of U.S. Provisional Application Ser. No. 60/186,230, with a filing date of Mar. 1, 2000, the disclosure of which is hereby incorporated by reference herein.

FIELD OF THE INVENTION

The present invention is directed generally to a method for collecting and preserving semen. More particularly, the present invention is directed to a method for collecting semen into a warmed extender solution having a particular volume. Most specifically, the present invention is directed to a method for collecting semen into a collection vessel having a semen extender maintained at a species appropriate temperature and having a particular chemical makeup. The method for collecting and preserving semen in accordance with the present invention results in greatly improved collected semen motility and longevity.

BACKGROUND OF THE INVENTION

Evidence suggests that semen has been collected for artificial insemination (AI) since the 1300's. It is held that Arabian tribes stole semen from rival tribes' stallions to inseminate their own mares and that the semen from a poor stallion was also used to inseminate the rival tribes' mares. The first documented use of AI was in the 1780's by the Italian physiologist, Spallanzani. His insemination of a bitch, with freshly collected semen, resulted in the production of three puppies. AI has continued to be developed as a tool in animal and human reproduction. Initially, a major problem with AI was that the collected semen had to be used the same day (and in cases such as with dogs, almost immediately) in order to achieve good results (i.e., pregnancy). In order for AI to develop to its full potential, a method had to be discovered to preserve semen for use at a later date.

The first successful, and by far still the most common, way to preserve semen for later use is with semen extenders. Semen extenders are used to provide nutrients for sperm metabolism, to carry additives such as antibiotics and cryoprotectants (for storage at lower temperatures), and to provide multiple breedings from one semen sample. In the 1930's, it was discovered that it was possible to use a buffered nutrient medium to extend the fertilizing life of semen for periods of up to three or four days. Extended semen can be maintained for a considerable length of time (times vary depending on the species) if the semen is chilled. Further, when a cryopreservative such as glycerol is added, extended semen can also be frozen and can remain viable (i.e., produce a pregnancy) for up to 20 years as shown in bovine semen.

Semen extenders have traditionally been added post-collection. After the semen is collected, the extender is normally added at a 1:1, 2:1, or 3:1 extender to semen ratio, depending on the initial motility, concentration, and species collected. In practice, the extender is added anywhere from a few minutes post-collection, up to approximately one-half to one hour post-collection.

Unprotected, freshly ejaculated semen loses motility and therefore fertilizing capability rapidly, rendering it virtually useless in a matter of a few minutes to a few hours (time varies depending on species). In some species, such as the canine, zero percent motility can be reached in less than one hour. This loss of fertilizing capability is even a problem with extended semen. If the extended semen is chilled, the reduction in motility and other semen parameters can be slowed, but not eliminated. The loss of motility and fertilizing capability is especially a problem for frozen-thawed semen. It is generally accepted that fifty percent or more of the initial motility will be lost during the freezing and thawing process.

From its earliest stages as a spermatogonia to its final maturation, which, from a biochemical standpoint, does not normally occur until after it has entered the female tract, the spermatozoon needs a constant supply of nutrients to maintain its metabolic activity and to undergo the processes necessary for fertilization of the ova. As spermatogonia develop into spermatozoa in the seminiferous tubules, their nutrient needs are provided by the Sertoli cells, also called nurse cells. These so-called "nurse cells" secrete fluids containing proteins necessary for the sperm cells to grow and to mature into the spermatozoa. They also supply some of the energy requirements of the sperm through the production of lactate, which is converted to pyruvate by the spermatid mitochondria.

As the spermatozoa are released into the lumen of the seminiferous tubules and continue their journey through the rete testes to the epididymis, they continue to be bathed in fluid rich in proteins, energy substrates such as glucose and lactate, and a variety of other substances. When the sperm cells reach the epididymis, they are still immotile. In the cauda epididymis, the sperm are concentrated and stored in a highly favorable environment. The epididymal cells secrete fluid that is low in pH and has a high potassium-to-sodium ratio. These conditions allow the sperm to be stored and matured and still remain viable for an extended period of time.

When the sperm are ready to be ejaculated, they are forced into the vas deferens and on into the urethra and then out of the body. Once the sperm reach the urethra the concentrated fluid in which they are contained is mixed with seminal fluid secreted by the accessory sex glands. The secretions of these glands contain buffers, nutrients, and a variety of other organic and inorganic substances. The buffers such as phosphates and carbonate buffers are essential for protection against pH shifts as the semen is deposited into the hostile environment of the female tract. In most species, the site of semen deposition, the vaginal vault, is extremely acidic. Further, as the sperm continue to metabolize, waste products, such as lactic acid, are produced which can lower the pH even more. The organic and inorganic ions such as sodium ($Na2+$), potassium ($K+$), and calcium ($Ca2+$) are necessary to initiate sperm motility and fertilizing capability. Other nutrients, such as fructose and sorbitol, are utilized by the sperm to meet energy requirements. Extenders were created in an attempt to hold the sperm in a favorable environment for cellular survival, while biochemically placing the cells in suspended animation (delaying their progression toward final maturation) until time for their use.

Since Spallanzani's first documented use of AI in the 1780's, artificial insemination has continued to develop its niche in reproduction. Because the raw (unprocessed) semen lost fertilizing capability rapidly after ejaculation, Spallanzani discovered that the semen had to be used soon after collection in order to achieve good results. It would be one hundred and fifty years before a method would be developed to extend the fertilizing life of spermatozoa after ejaculation.

With the development of semen extenders, semen could be preserved for use many hours, or even days, post-ejaculation. First described in the 1930's, it was discovered that it was possible to use a buffered nutrient medium to extend the fertilizing life of semen for up to three or four days. Extenders are used in an attempt to hold sperm in optimal conditions until their use and also allow for multiple breedings from one semen sample.

In order for a semen extender to be effective, it must contain a number of ingredients. It must buffer the semen against shifts in pH due to the continual metabolic activity of the sperm during storage. It must also maintain an isotonic environment. If the extender is hypertonic, the sperm will shrivel and die. If the solution is hypotonic, the sperm will swell and burst. A number of ingredients have been used to meet these requirements. The first successful buffer to be used in a semen extender was the phosphate buffer. Although the phosphate buffer worked, the sodium citrate buffer soon replaced it, because when mixed with egg yolk (a common nutrient in semen extenders) the mixture remained transparent. A variety of other buffers and various combinations of these buffers are now available. Some of these buffers are the tris buffer solution, the tes buffer, the test-yolk buffer (combined tes and tris buffers with egg yolk), and tris-citrate buffer. Regardless of which buffer is being used, all are added in the proper concentrations to not only buffer the solution, but also to maintain the isotonic nature of the extender.

Semen extenders must contain adequate nutrients for sperm to metabolize during storage. A variety of substances fill this need. Milk and egg yolk are common protein sources. A third protein source is irradiated bovine albumin.

Simple sugars are added to provide the sperm with energy. Fructose, glucose, sucrose, sorbitol and pyruvate have all been used in semen extenders as sources of energy. Pyruvate, by its chemical nature, is the energy substrate most easily utilized by the sperm. However, it is not the most common energy source. The most common energy substrate found in commercial semen extenders is fructose. Its ability to easily be converted to pyruvate within the sperm mitochondria and its cost effectiveness make it an ideal source of energy.

In addition to their roles as nutrient sources, proteins also help fulfill another requirement of the semen extender by serving as cryoprotectants. Unprotected, the membranes of the spermatozoa undergo configurational changes as the temperature is lowered (cold shock). However, the lecithin, lipoproteins, and phospholipids from the protein source provide protection from cold shock. As the semen is lowered from body temperature to 5° C., the temperature at which fresh chilled semen is held during storage, the sperm will undergo cold shock if not protected. When properly prepared, chilling to this temperature keeps the semen viable for a longer period of time than if kept at approximately room temperature (15–20° C.). Further, non-protein cryoprotective agents must be employed if the semen are to be frozen. This will be discussed in detail below.

The final ingredient in most semen extenders is an anti-microbial agent. The anti-microbial agent is essential for reducing microbial contamination and preventing the spread of diseases that can be transported in the semen. Through their control of venereal diseases, these agents have also been shown to improve conception rates. Some common antibacterial agents are penicillin, streptomycin, lincomycin, and gentamicin.

When an extender is to be used as the base media for freezing and long-term storage of semen (cryopreservation), an additional cryoprotective agent must be added to protect spermatozoa from ice crystal formation. When semen is frozen without a cryoprotectant, the ice crystals that form during the freezing process puncture the cell membrane and result in cell death. By using a cryoprotectant such as glycerol or DMSO (dimethylsulphoxide), a large portion of the intracellular water is displaced by the cryoprotectant; therefore, cellular damage due to ice crystal formation is largely prevented.

Semen extenders have continued to be used since their inception and a variety of extenders and cryoprotectants are now available commercially. These products fall into three basic classes based on their protein source (egg yolk, milk, or albumin). The egg yolk based extenders are used in many species, including cattle, sheep, dogs, and humans. Milk based extenders are used almost exclusively in the horse. The third class of extenders, serum albumin based extenders, are used in species such as dogs, exotics and humans.

Artificial insemination has been used for several centuries. However, it was not until the early 1900's, when semen extenders were developed, that semen could be stored and used at a time other than immediately after collection. The traditional method of extending semen was, and still is, to add the extender anywhere from a few minutes up to one hour post-collection. While this method does help preserve semen for use at a later time post-collection, data from this experiment suggests it is not the most efficient method.

Semen collection can be performed in a variety of ways depending on the species. Methods include the artificial vagina (AV), electro-ejaculation, digital manipulation and masturbation.

The first artificial vagina was developed at the University of Rome in 1914 for use in the dog. Russian scientists developed other AV's for use in larger species such as the horse in 1933. Today's AV's, which vary in size and shape depending on species, consist of a tapered collection sleeve, in which the penis is placed. Attached to the tapered end is a collection container. Most AV's attempt to simulate natural copulation by providing suitable temperature, pressure and lubrication to induce ejaculation.

The electro-ejaculator was developed in the 1940's. It consists of a probe that is placed into the rectum of the male to be collected. A low-voltage current (0 to 30 volts with 0.5 to 1.0 amperage) is passed through the probe, stimulating ejaculation. This method is often used in bovine and ovine. The electro-ejaculator has also been used in humans with lower-body paralysis in order to obtain an ejaculate. While this method of collection is effective, it can produce lower quality semen samples when compared to the artificial vagina or digital manipulation. The electro-ejaculator should never be used in the equine due to possible tearing of the rectal tissue.

Digital manipulation is another method used for semen collection. This technique involves the physical manipulation of the penis by the collector to obtain an ejaculate. This method can be used alone with a collection container or combined with an artificial vagina. This technique is commonly used in the porcine and the canine.

The most common method for semen collection in the canine is with the use of an artificial vagina and digital manipulation. This technique involves the collector utilizing digital stimulation to encourage the dog to extend his penis and ejaculate into the artificial vagina. The index finger and thumb are placed in a u-shape behind the bulbus glandis, which helps to give the male the sensation of being "locked". It is helpful with some animals to allow the dog to step over the collector's arm, simulating the natural tie. Depending on the individual animal, variations in pressure, friction, and movement may be necessary to obtain an ejaculate.

Regardless of which method is being used to obtain a semen sample, all must use some type of collection container. With the traditional collection methods, the collection containers (in the case of the canine, usually a plastic centrifuge tube) do not have any media placed in them prior to collection. After the semen is collected the extender will be added anywhere from a few minutes, up to one hour post-collection, depending on the protocol being used. While this method works and continues to be used today, it may not be the most efficient method.

Sperm are especially susceptible to changes in temperature. With natural service, semen is ejaculated into the warm moist environment of the female tract. However, with the traditional method of semen collection, semen is collected into a dry container where variations in temperature can be a real problem, especially if the collection room is cold. When using a dry collection tube, the outside air temperature is quickly transmitted to the semen sample. One study on mouse spermatozoa showed that sperm collected at 0° to 4° C. had significantly lower motility than that of sperm collected at 22° C. Occasionally, attempts to maintain the temperature of the collection tubes have been performed. Although attempting to maintain the temperature of the collection tube is of some help, the semen is still being shocked. The semen is coming in contact immediately with the collection container and any temperature variation can still be a problem.

Sperm are also susceptible to shifts in pH. While semen extenders do contain buffers, the semen may not come in contact with these buffers until well after collection. The semen being collected into the dry collection tubes does not allow the sperm to be buffered immediately. Because sperm are continually metabolizing, the pH will quickly change in the absence of a buffer.

SUMMARY OF THE INVENTION

It is an object of the present invention to provide an improved method for collecting and preserving semen.

Another object of the present invention is to provide a method for collecting semen into a collection vessel having a particular extender solution volume.

A further object of the present invention is to provide a method for collecting semen into an extender solution maintained at a desired temperature.

Still another object of the present invention is to provide a method for collecting semen into an extender solution having a particular composition.

Modifying the way semen is collected and extended lessens the problems of reduced motility and fertilizing capability seen in chilled extended semen. Sperm are easily susceptible to shock due to temperature and pH shifts. This shock to the sperm can result in decreased motility and other semen parameters and therefore decreased semen life. Protecting semen from temperature and pH shock upon collection would extend the functional life and fertilizing capability of the spermatozoa. The method of semen collection and extension has been modified. A portion of the extender is added to the collection vessel prior to semen collection, in an attempt to lessen or prevent shock of the spermatozoa.

The collection of semen samples into warmed extender media protects spermatozoa from the initial cold and pH shock that can occur when traditional collection and extension methods are used. By collecting directly into the semen extender, the spermatozoa are immediately placed into a buffered environment, lessening the chances of pH shifts. Further, when the extender is warmed to the body temperature appropriate for the species being collected, the problem with temperature shock is also lessened. While extenders have been added to the collection vessel prior to collection in selected species, for example, for the treatment of subfertile animals and in humans for the treatment of anti-sperm antibodies, this technique has never been used with animals having normal fertility nor as a routine methodology in humans.

Data obtained from experiments demonstrates that collection into warmed extender media lessened the change of temperature and pH shock to the spermatozoa compared to that reported in previous studies, as shown by the improved semen parameters. This modification to the collection/extension of semen in accordance with the present invention allows for improved preservation of spermatozoa over time when compared to traditional methods. Data analysis clearly shows that collecting semen into warmed extender media improved the semen parameters evaluated. Specifically, the functional life span of the spermatozoa, measured as motility, was significantly increased in the treatment group as compared to the control (time to zero motility).

Some dogs were classified as "Tolerant" and "Intolerant" depending on their tolerance to traditional methods of semen collection. When comparing the "Tolerant" and "Intolerant" groups, both groups demonstrated improvement in motility in the treatment group. However, semen collected from those animals that were "Intolerant" to the traditional collection method appeared to demonstrate the most improvement. By collecting into the warmed extender, the temperature remained constant preventing cold shock to the spermatozoa. The spermatozoa also came in contact with the buffers of the extender immediately upon collection which helped to prevent shifts in pH.

The treatment group maintained motility significantly longer than the control. This held true for both the "Tolerant" and "Intolerant" groups, with the "Intolerant" samples demonstrating the greatest response to the methods of this disclosure. This improved motility over time led to the improvement seen in the time to last full insemination. Further, times to full acrosome reaction were delayed in the treatment group. By maintaining a greater percent of motile (and therefore viable), non-acrosome reacted sperm, the treatment group maintained a full insemination dose for a greater length of time as compared to the control. By calculating the available sperm pool (total motile sperm per ejaculate), it was possible to observe that in animals with good concentration and volume had a greater number of inseminations upon collection and maintained at least one full insemination dose much longer due to the treatment. In animals that had lower concentrations and/or volumes, it was possible to get an insemination by using the treatment where no insemination would have been available using traditional methods.

By utilizing the collection method of the present invention in the collection/extension procedure, it is possible to improve semen parameters in both the "Tolerant" and "Intolerant" animals, with the "Intolerant" animals appearing to demonstrate the most improvement. Semen from animals with a good volume and concentration can be extended and maintained for a longer period of time as compared to traditional methods, allowing for improved ability in shipping fresh-extended semen. Animals that would not have an adequate semen sample for insemination, when using traditional methods, would now have to ability to be used for AI.

BRIEF DESCRIPTION OF THE DRAWINGS

While the novel features of the method for collecting and preserving semen in accordance with the present invention are set forth with particularity in the appended claims, a full and complete understanding of the invention may be obtained by reference to the detailed description of the preferred embodiment, as is set forth subsequently, and as illustrated in the accompanying drawings, in which:

DETAILED DESCRIPTION OF THE INVENTION

Figure 1:
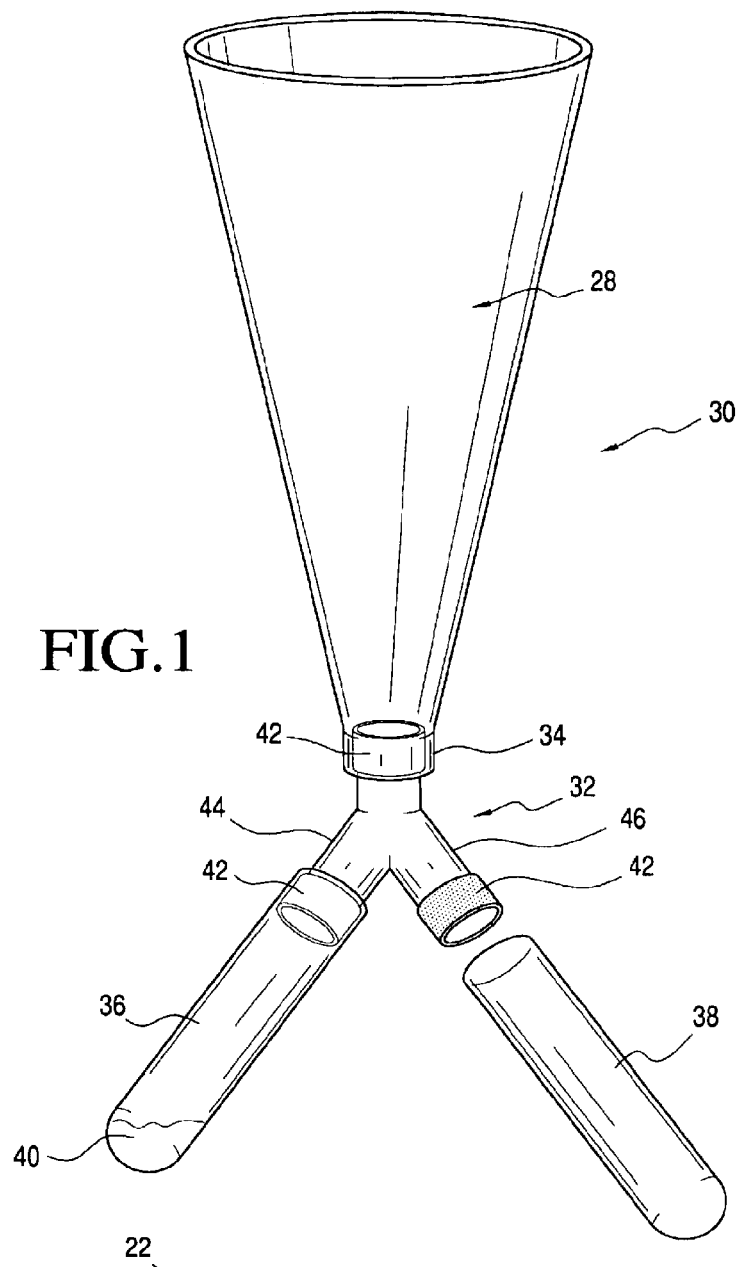
FIG. 1 is an exploded perspective view an artificial vagina utilizing a collection vessel in accordance with the present invention.

While some current techniques of semen collection attempt to maintain the temperature of the artificial vagina for the male's comfort, only a few attempt to insulate the collection container (porcine technique) and none attempt to maintain the pH of the specimen. Maintaining the spermatozoa at its preferred physiological temperature and a pH close to 7.4 will maintain the spermatozoa in optimum condition during collection, processing and in preparation for storage, and will improve post-storage semen parameters.

The collection system of the present invention has been constructed to answer the physiological needs of the spermatozoa at the time of collection and lessen or prevent shock damage which would lead to decreased fertility to the spermatozoa. This collection system could be used in any mammalian specie, including domesticated and non-domesticated animals, as well as in humans, and with any existing extender/cryoprotectant.

In accordance with the present invention:

1) the samples of semen are collected into a measured volume of the protective agents which protective agent or extender volume is provided in the range of approximately 20% to 100% of the total expected semen volume that will be placed in the specie-specific collection container, 2) the sample/media complex is maintained at physiological temperature, 32–38° C.; specific to each specie, and 3) only the sperm-rich fraction of the ejaculate are collected. A series of specie specific collection devises to allow for a true division of the ejaculate, either into fractions or a true-split ejaculate have been developed. These devises allow easy collection of the sperm-rich portion of the ejaculate while minimizing contaminating by sperm-poor and gel fractions.

In preparation for extension/cryopreservation, the specie appropriate semen collection device is prepared. The extender/cryoprotectant is warmed to −3 to 0° C. of the expected semen temperature upon ejaculation. Further, the collection vessel is warmed to the same temperature, A measured volume of the specie-appropriate extender/cryoprotectant in the volume range of 20–100% of the expected sperm-rich volume is added to the collection vessel. This media volume is set forth in Table 1 as follows:

TABLE 1

Specie-Specific Volumes of Extender/Cryoprotectant Added to the Collection Vessel Prior to Collection for Common Domestic Mammal Species and Humans

| Specie | Media Volume (ML) | % of Expected Volume |
|---|---|---|
| Bovine | 1–2 | 20 |
| Canine | 1 | 20–100 |
| Equine | 10–15 | 20–50 |
| Ovine | 1 | 100 |
| Porcine | 20–50 | 20–50 |
| Human | 1 | 20–100 |

Where appropriate, the collection vessel is attached to the artificial vagina and the sample collected using the accepted technique for that specie. Once the collection is complete, the size of the ejaculate is determined (Total volume minus the extender/cryoprotectant added prior to collection). Additional warmed media is added to dilute the semen sample to its final concentration (1:1 or 1:2 for cryopreservation and 1:2 or 1:3 for extension; specie specific), and processed using standard industry techniques.

A proprietary media based on the specific physiological needs of a motile spermatozoa for each species has been developed. This will be discussed shortly.

Figure 2:
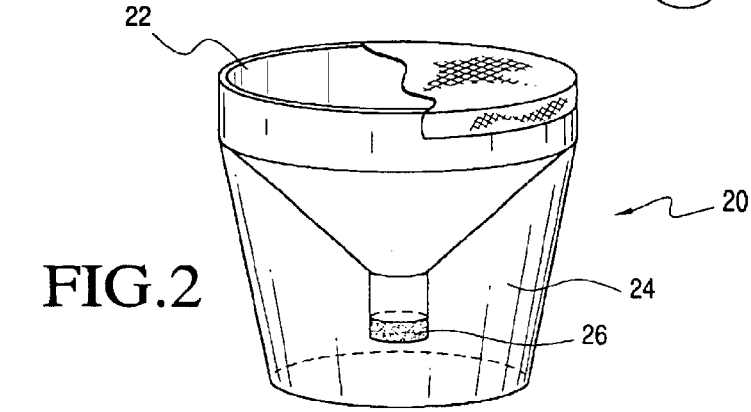
FIG. 2 is a perspective view showing a modified collection vessel for species not collected by the artificial vagina shown in FIG. 1.

Collection techniques vary widely between species, therefore adding media to the collection vessel prior to collection presents unique problems which are specie specific. However, the collection vessels used to collect domestic mammal species and human fall into three general types as outlined in Table 2. The artificial vagina is shown in FIG. 1 while the warmed collection vessel is depicted in FIG. 2.

TABLE 2

Collection Techniques

| Technique | Specie |
|---|---|
| Artificial Vagina | Bovine, Equine, Canine |
| Warmed Collection Vessel | Porcine |
| Dry, Room Temperature Collection | Ovine, Bovine, Human |

The porcine is collected by digital manipulation into a warmed collection vessel generally at 20, as depicted in FIG. 2, which has a mouth opening 22 covered with gauze to strain out the gel fraction of the ejaculate. While the vessel 20 is generally warmed by an outer warmed chamber 24, the vessel itself is dry before collection. The appropriate desired volume of extender media 26 is simply added to the vessel prior to placement of the gauze. Unlike, the open, warmed, vessel 20 of the porcine, the artificial vagina, generally at 28 shown in FIG. 1, represents a closed system 30 for semen collection. Once the male's penis is placed into the system 30, all fluids ejaculated are routed to the collection vessel. While gel can be filtered similarly to the open container by placing gauze at the collection vessel opening, it is difficult to eliminate the sperm-poor fractions of the ejaculate. However if a biocompatible y-tube 32 is placed at the junction 34 of the artificial vagina 30 and the collection vessel or vials 36 and 38, it is possible to route the sperm-rich portion in one direction and the sperm-poor fraction in the other. The warmed media 40 can then be placed in the collection vessel 36 used for the sperm-rich fraction.

The collection vessel shown in FIG. 1 includes the artificial vagina 30 connected to a y-tube 32. Latex gaskets 42 are suitable for securing a tight fit between the artificial vagina 30 and the y-tube 32. Other known sealing agents may be used. It is preferred that the sealing agent bond the components together sufficiently to allow the assembled parts to remain integral during manipulation of the animal, but preferably it still is possible to disassemble the components after collection of a semen sample. Collection vessels, for example, vials 36 and 38 are connected to the ends located near the split ends 44 and 46 of the y-tube 32. Preferably the collection vials 36 and 38 fit over the outer diameter of the ends 44 and 46 of the y-tube 32. Likewise, in one embodiment of this invention, the outer diameter of the smaller opening of the artificial vagina is slightly less than the inner diameter of the opening of the y-tube 32 connected to the artificial vagina. Alternatively, the smaller opening of the artificial vagina may fit over the y-tube 32.

Finally, in those species which have traditionally been collected into an open, dry, container that has been maintained at room temperature such as the container 20 of FIG. 2, it is necessary to change the shape of the container to accommodate the inclusion of a volume of extender media appropriate for each specie, such volume typically being between 1 and 10 mL. Because of the small collection volumes, it is also necessary to place insulation around the vessel to prevent cooling. However, the open end 22 of container 20 must be large enough to accommodate the free end of the penis. A collection device capable of both is shown in FIG. 2.

It is not unknown for the collection process to take up to 45 minutes. The insulation is chosen to minimize temperature variation of the collection vessel and added extender solution such that the temperature of the collection vessel 26 and added extender solution does not vary more than 2 or 3° C. over a period of time up to 45 minutes. Of course, it is understood that the extender solution and the collection vessel are initially within 2 or 3° C. of an initial temperature appropriate for the species being collected.

Figure 3:
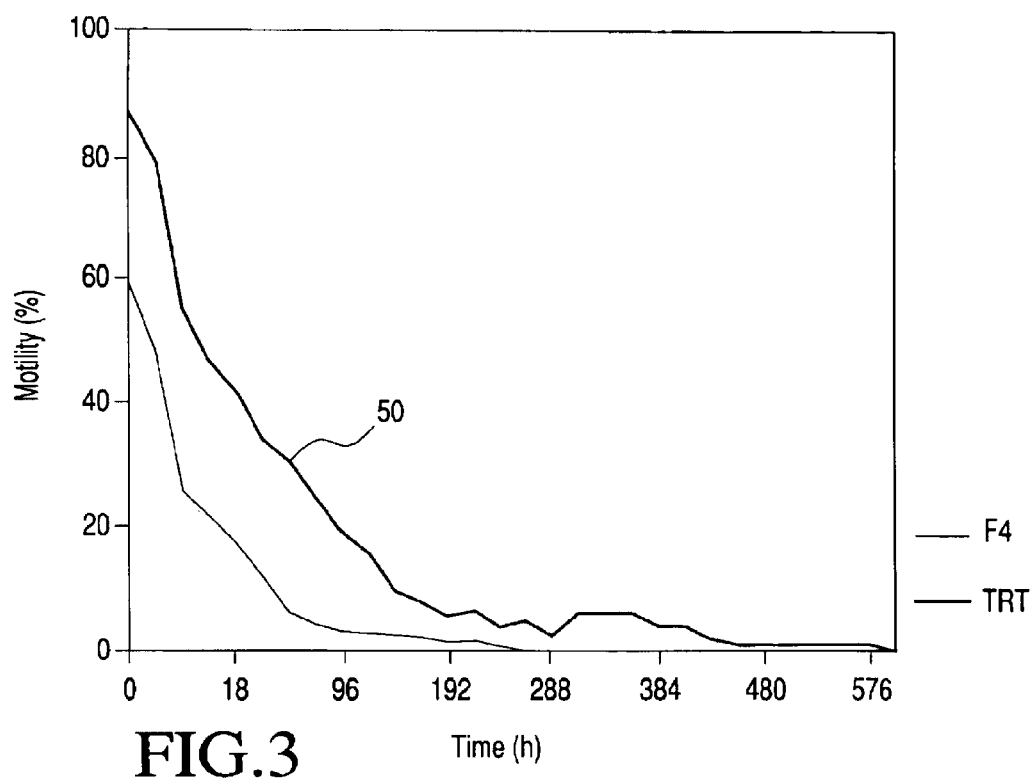
FIG. 3 is a graphical showing of the comparative motility of canine semen obtained by the methodology of the present invention compared with motility data of semen obtained by tradition methods.
Figure 4:
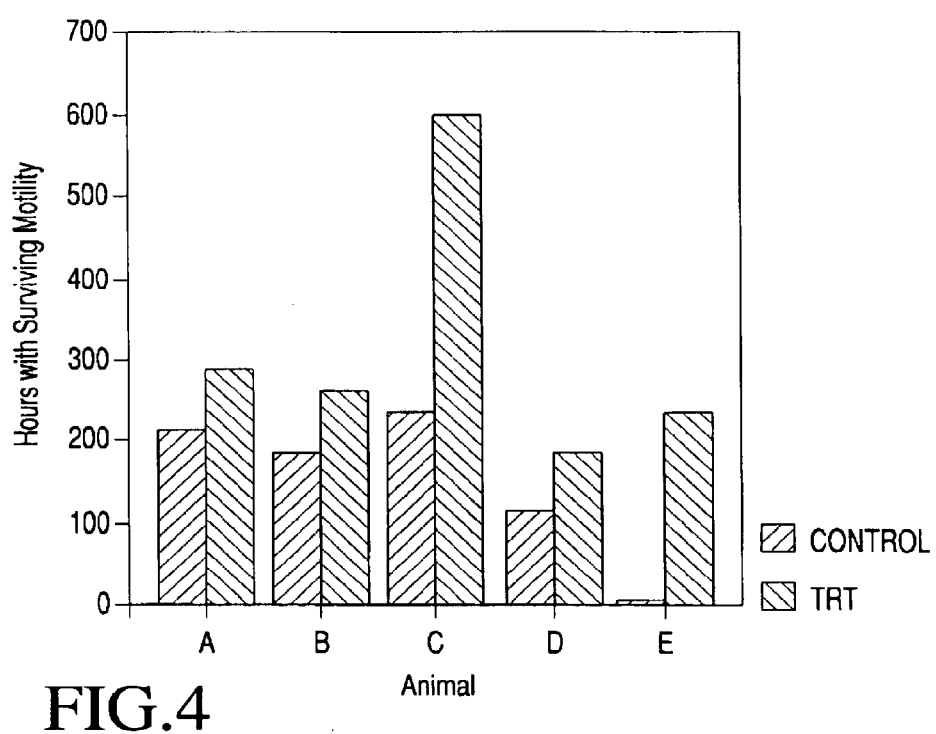
FIG. 4 is a graphical showing of the survival time of canine spermatozoa from five different animals using semen treated by the methodology of the present invention compared with semen treated by tradition methods.

Preliminary data from the canine, a specie resistant to current technology, indicates that the inclusion of the protective agents prior to collection maintains all semen parameters (motility, viability, etc . . . ) at higher levels than semen prepared in the tradition fashion. Canine semen were prepared for extension using the commercially available extender, Androhep (Minitube of America; Verona, Wis.). Split ejaculates were collected using the y-tube described above. In all cases, the ejaculate fraction collected into warmed extender maintained increased spermatozoa activity when compared to the fraction collected into a dry container. This is depicted in FIG. 3 with the line 50 identifying the improved semen obtained in accordance with the present invention.

Further, as this technique can not be detrimental to semen quality; we have used the technique has been used, with permission of the dogs' owners but without disclosing the technique, in the breeding of six dogs. Semen were prepared for extension as described above or for cryopreservation using the cryoprotectant, Freezing Medium-TEST Yolk Buffer (Irvine Scientific; Santa Ana, Calif.). Breedings to date have resulted in the production of five litters.

Figure 5A:
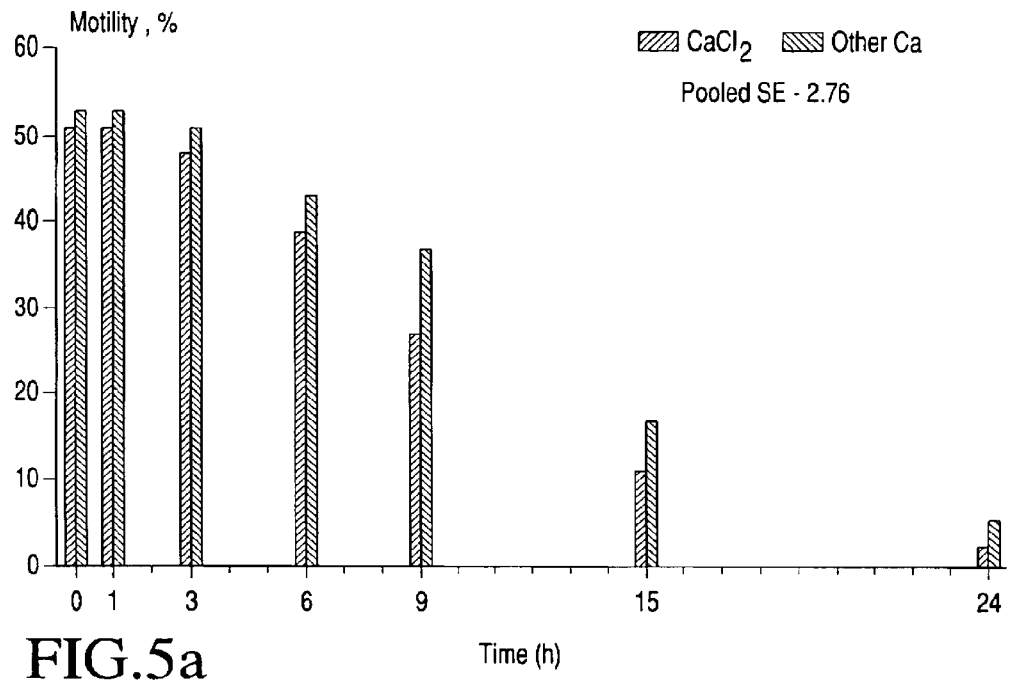
FIG. 5a is a graphical showing of the least-squares mean values of percent motility of porcine spermatozoa using semen treated by the methodology of the present invention compared with semen treated by tradition methods.
Figure 5B:
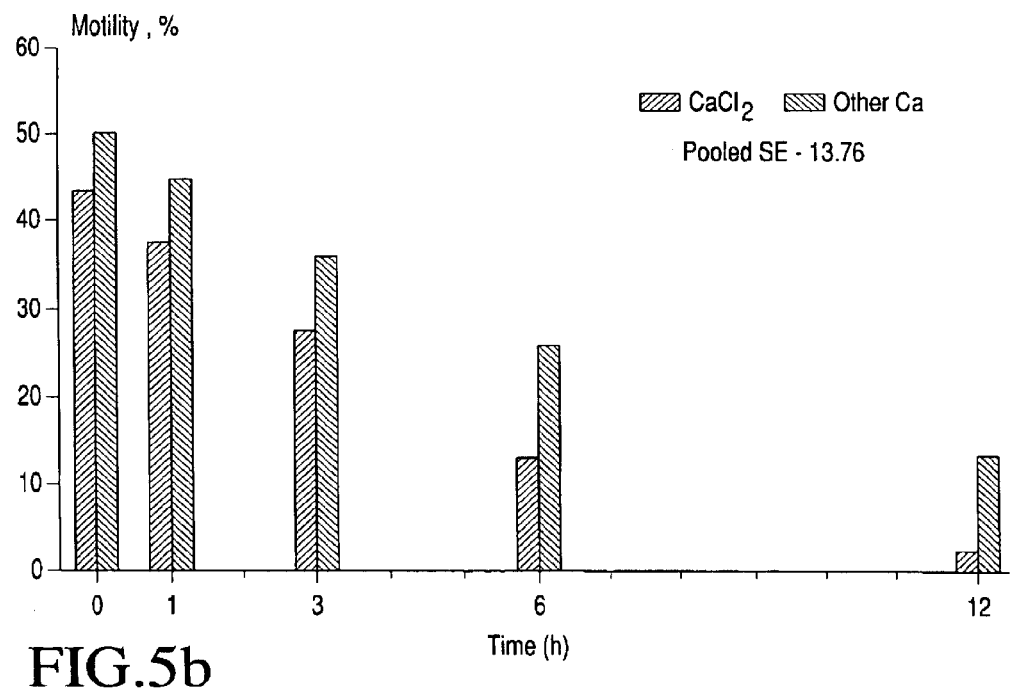
FIG. 5b is a graphical showing of the least-squares mean values of percent motility of human spermatozoa using semen treated by the methodology of the present invention compared with semen treated by tradition methods.

Extenders represent an osmotically balanced salt solution, containing both an energy source (sugar), and a protein source [for both metabolites and as a high temperature (0–5° C.) cryoprotectant]. Cryopreservatives add one of several cryoprotective agents to this base media in order to protect the spermatozoa at low temperatures −30 to −196° C. Ringer's Lactate has many attributes of an extender. It is an osmotically balanced salt solution (as per its design as a fluid volume replace solution following dehydration, surgery or injury). It also has two sugar sources, sodium lactate and fructose. Further it has calcium, an essential element for sperm motility. However, it lacks the protein source of the classical extenders and earlier work suggests high levels of chloride may be detrimental to spermatozoa function. Short term semen quality (culturing 1–24 hr) can be improved simply by substituting a variety of calcium compounds into the Ringer's lactate to replace the calcium chloride. These quality improvements are shown in FIGS. 5a and 5b. Of the calcium compounds tested, semen function was maintained best in calcium phosphate, calcium carbonate, and calcium gluconate. With the addition of a protein source, these modified Ringer's Solutions function as extenders, and with the addition of a cryoprotective agent they also serve as cryoprotective media and further improve the described collection process. Formulation of the modified compounds are listed in Table 3.

TABLE 3

Reformulation of Ringer's Lactate Solution for Use as a Semen Extender (mg/100 mL Water)

| | CaCl$_2$ Substitution with | | |
|---|---|---|---|
| Chemical | CaCO$_3$ | Ca(H$_2$PO$_4$)$_2$ | Ca gluconate |
| NaCl | 600 | 600 | 600 |
| Na lactate | 310 | 310 | 310 |
| KCl | 30 | 30 | 30 |
| Fructose | 20 | 20 | 20 |
| CaCO$_3$ | 40 | — | — |

TABLE 3-continued

Reformulation of Ringer's Lactate Solution for Use as a Semen Extender (mg/100 mL Water)

| Chemical | CaCl$_2$ Substitution with | | |
|---|---|---|---|
|  | CaCO$_3$ | Ca(H$_2$PO$_4$)$_2$ | Ca gluconate |
| Ca(H$_2$PO$_4$)$_2$ | — | 82 | — |
| Ca gluconate | — | — | 154 |
| Protein Source* | 0.1 | 0.1 | 0.1 |

*protein sources will vary with specie and will be those currently used (egg yolk, milk, bovine albumin).

Unprotected, freshly ejaculated semen loses motility and therefore fertilizing capability rapidly, rendering it virtually useless in a matter of a few minutes to a few hours (time varies depending on species). In some species, such as the canine, zero percent motility can be reached in less than one hour. This loss of fertilizing capability is even a problem with extended semen. If the extended semen is chilled, the reduction in motility and other semen parameters can be slowed, but not eliminated. The loss of motility and fertilizing capability is especially a problem for frozen-thawed semen. It is generally accepted that fifty percent or more of the initial motility will be lost during the freezing and thawing process.

In theory, modifying the way semen is collected and extended may lessen the problems of reduced motility and fertilizing capability seen in chilled extended semen. These results should also apply to frozen-thawed semen. Sperm are easily susceptible to shock due to temperature and pH shifts. This shock to the sperm can result in decreased motility and other semen parameters and therefore decreased semen life. In theory, protecting semen from temperature and pH shock upon collection would extend the functional life and fertilizing capability of the spermatozoa. a portion of the extender is added to the collection vessel prior to semen collection, in an attempt to lessen or prevent shock of the spermatozoa.

In this invention, extension of the functional life span and fertilizing capability of semen has been attained through a modification of the traditional collection/extension method. Using the canine as a model, semen were collected into a measured amount of warmed extension media (~20% by volume of the expected volume of ejaculate=1 ml) to determine if this method improved the life span and/or the fertilizing capability of the semen over the traditional method.

The canine was chosen for the model for a number of factors: (1) Canine sperm are one of the more difficult cell types to maintain for any length of time outside the body. Therefore, if semen parameters can be improved in the canine through the modification of semen collection/extension, then theoretically the technique should work well in other species including humans, (2) Canine semen is similar in volume, concentration, and sperm physiology to humans and works well as a model, (3) Canines are relatively easy to handle and collect, (4) And finally, there is a ready supply of dogs available in the community with known histories and therefore, there was no need to purchase and house test animals.

Prior to collecting an animal, basic information such as name, age, breed, AKC registration number, owner's information, and date collected were recorded. In order to meet the requirements set by the Animal Care and Use Committee, all collections were made under the supervision of a local veterinarian.

It was necessary to collect semen so that both the control and treatment samples were collected simultaneously from the animal. This method of collection was necessary in order to eliminate the variation that can be seen between different collections, or even different collection fractions (traditional split collection), within the same animal. No traditional collection device allowed for this type of collection. Therefore, it was necessary to develop a collection device that could be used to fulfill this need.

The modified artificial vagina with a biocompatible Y-tube as shown in FIG. 1 and as previously described allowed for a true split collection. This allowed one ejaculate from an animal to serve in both the control and treatment arms of the study.

Collection of the semen samples was done using digital manipulation and the modified artificial vagina. Prior to collection the centrifuge tubes used to collect the semen were prepared. One tube was labeled control and no special procedures were taken. The other tube was labeled treatment and a measured amount (1 ml) of 37° C. semen extender was placed into the tube. This tube continued to be maintained at the 37° C. temperature.

The collection involved two individuals, one to collect the dog (collector) and one to manipulate the collection device (handler). The dog was encouraged to extend his penis and then the penis was placed into the lubricated AV. Using digital manipulation, the collector manipulated the dog until initial ejaculation. As the dog ejaculated the handler guided the Y-tube portion of the AV so as to collect relatively equal amounts of semen into each side of the collection device. Once the dog had finished ejaculating the AV was removed. The extension of the treatment sample was then completed immediately using a 2:1 extender to semen ratio by volume. The control sample was held fifteen minutes post-collection before extending at the same ratio. This delay was chosen based on common veterinary practices.

Semen samples were evaluated at zero, one, six, twelve, eighteen, and twenty-four hours post-collection and at twenty-four hour intervals there after, until zero percent motility was reached. After the one-hour evaluation, semen was chilled to 5° C. and stored. For the subsequent evaluations, a small amount (~25 ml) of semen was removed and warmed in a 37° C. waterbath. Selected semen parameters were recorded at each time interval for both the treatment and control groups during the course of the experiment. Evaluations of a treatment ended when motility in that sample reached zero percent. The parameters evaluated included: volume, concentration, motility, forward progression, acrosome reaction, viability, and morphology. All standard semen parameters were evaluated on a Nikon Alphapot microscope equipped with phase optics (Nikon Inc.; NY, N.Y.). Acrosome measurements were made on a Zeiss Standard microscope equipped with fluorescence and cubes (Carl Zeiss Inc., NY, N.Y.).

Volume

The initial total volume of semen was recorded upon ejaculation. It included the volume in both the control and the treatment (minus the volume of extender added prior to collection) arms of the study. The total volume of ejaculate was used to calculate the available sperm pool (discussed below) for both the control and treatment groups.

Concentration

A slide designed to hold a measured volume of semen (3 microns; Microcell; Conception Technologies, San Diego, Calif.) was used along with an eyepiece micrometer to determine the concentration. When viewed under the microscope at 100× magnification, the number of sperm in ten blocks of the micrometer (selected at random) is used to calculate the number of sperm per milliliter of an un-extended sample. Because the semen was extended at a 2:1 semen to extender ratio, it was necessary to multiply the observed count by three in order to calculate the actual concentration. The concentration was recorded in number of sperm per milliliter of ejaculate. The concentration was averaged across time intervals for both the treatment and control samples. These averages were used to calculate an average concentration across both the treatment and control samples. This pooled average concentration was then used to calculate the available sperm pool (see below).

Motility

Because motility is one of the major criteria used in evaluating the fertilizing capability of sperm, the percent motile sperm was recorded. It is necessary for sperm to be motile in order to cross the zona pellucida and fertilize the oocyte. Once motility is lost, the sperm lose the ability to fertilize an ovum without assistance from techniques such as Intercytoplasmic Sperm Injection. Therefore, the logical end for the evaluations was when samples reached zero percent motility.

Using a Microcell slide and 100× power, a total of one hundred sperm were counted. The number of moving sperm per one hundred gave the percent motility. All counts were made manually.

Forward Progression

At each time point the forward progression of the motile sperm was evaluated using a five-point scale as follows: 5+ sperm moving rapidly in a forward direction across microscope viewing field (in approximately one second or less), 4+ sperm moving steady but slower in a forward direction across the microscope field, 3+ in a rapid side-to-side motion with slow forward progression, 2+ sperm moving in a side-to-side direction with no forward motion or in a circular or irregular pattern, 2+ sperm moving slightly side-to-side or in place with slight tail movement, and 0 no movement detected.[16]

Acrosome Reaction

In order for sperm to be able to fertilize the oocyte, they must first undergo and the acrosome reaction. This is a process where the acrosome cap of the sperm head dissolves and releases enzymes which allow the sperm to bind to the zona pellucida of the oocyte.

Figure 6:
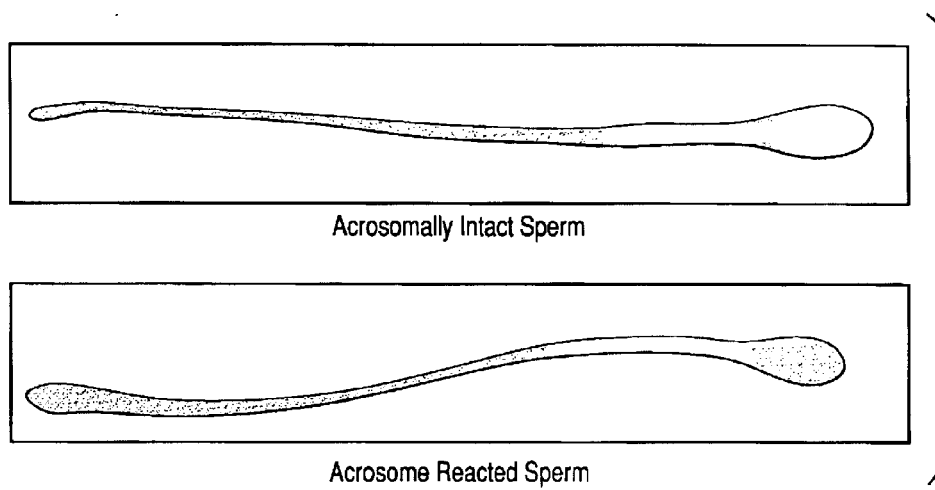
FIG. 6 is a depiction of acrosomally intact sperm and acrosome reacted sperm.

At each time point, the acrosome reaction was evaluated using a Chlorotetracycline stain. When viewed under a fluorescent microscope, equipped with a 520 μm excitation filter and a 570 μm barrier filter, the intact acrosome cap appears a fluorescent yellow. If the cap is visible, the sperm has not undergone the acrosome reaction. Both acrosome reacted and dead sperm (sperm which have lost the selective permeability of their membranes) loose their acrosomal cap and therefore appear faded. In this context, please refer to FIG. 6. Because the acrosome reaction must not occur until the sperm are in the proximity of the oocyte, during storage it is desirable that the acrosome caps remain intact. Therefore, the percent of non-acrosome reacted sperm was recorded at each time point. These numbers were then used in the calculation of the available sperm pool.

Slides were prepared by mixing 0.5 microns of semen with 1 micron of Chlorotetracycline stain. A coverslip was placed on the slide and the slide was viewed immediately using oil immersion under 1000× power. A total of one hundred sperm were counted and the percentage of non-acrosome reacted sperm was recorded.

Available Sperm Pool

The available sperm pool was calculated in order to determine the number of motile, non-acrosome reacted sperm available for insemination and the number of insemination dosages at any given time point. It was calculated by multiplying the total volume by the pooled average concentration, the percent motile sperm, and percent of non-acrosome reacted sperm (example: 2 ml×100 million/ml×50% motile×50% non-acrosome reacted=50 million available sperm). The available sperm pool was then divided by the number of sperm needed per insemination (number varies depending on species) in order to determine the number of inseminations available. In the canine, there has been a great deal of controversy on the number of sperm needed per insemination to achieve a good pregnancy rate. Numbers range from 20 million to 200 million motile sperm per insemination. Based on communication with a local veterinarian (who is a canine reproductive specialist) and the fact that the number of non-acrosome reacted sperm (along with percent motile sperm) was included in calculating the available sperm pool, 60 million motile, non-acrosome reacted sperm was used as the insemination dosage needed to achieve a pregnancy in the canine. Survival time to last full insemination (last time point with at least 60 million motile, non-acrosome reacted spermatozoa) was calculated and compared between the control and treatment groups.

Viability

The viability or number of live cells was recorded at each time interval for both groups. Viability was accessed using Touladine Blue as a viability stain. Live sperm do not allow the stain to penetrate the cell membrane, while dead sperm (sperm which have lost the selective permeability of their membranes) accept the stain. Therefore, when viewed under the microscope at 100×, the live sperm appeared clear, with a bluish purple halo, while the dead sperm appeared completely bluish purple.

Slides were prepared by mixing 0.5 microns of semen with 0.5 microns of Touladine Blue stain and smearing the mixture across the slide. The slides were then dried on a slide warmer plate at 56° C. A total of one hundred sperm were counted and the number of live sperm gave the percent viable.

Morphology

Morphology was recorded at the initial time point, approximately one-half way through the evaluations, and when zero percent motility was reached, for both the treatment and control samples by three investigators, to verify that morphology did not change due to treatment. Morphology was not used in calculating the available sperm pool as the number of normal sperm fell within the acceptable range of sixty to eighty percent or greater.

The morphology slides were prepared by smearing 0.5 microns of semen across a slide. The slides were then dried on a slide warmer plate at 56° C. Dried slides were then stained using an Eosin-Hematoxylin stain using the following steps; (1) slides were dipped ten times in Methanol, (2) slides were then transferred and dipped into Eosin ten times, (3) slides were transferred and dipped ten times in the Hematoxylin, (4) slides were then rinsed by dipping ten times into de-ionized water, and finally, (5) slides were dried on a slide warmer plate at 56° C. A total of one hundred sperm were counted and the number of head, mid-piece, and tail defects were noted at each evaluation along with the percentage of normal sperm. This was done to confirm that there was no change in morphology over time.

Experiment Design

The study was designed as a split-plot with repeated measures having a specific end point. Because a portion of the same ejaculate from each dog was represented in both the treatment and control arms of the study, the design was a true split plot. The same ejaculate was evaluated over time, resulting in the repeated-measures factor. However, individual animals had a significantly different number of repeated measures due to the fact that when samples reached zero percent motility the data collection ended. Because of the specific ending point being zero percent motility, the zero was an actual number and was included in the data analysis. An alpha level of 0.05 was set for consideration of whether a statistical difference was detected.

Sample Numbers

A total of ten animals were used in the study. The criteria for participation were that the dogs had sufficient volume so the ejaculate could be represented in both the treatment and control arms of the study and that there was motile sperm upon ejaculation. Having ten dogs represented in each group along with the repeated measures factor allowed for more than ample numbers of observations to show a statistical difference.

Data Analysis

All data were analyzed using the Statistical Program for the Social Sciences (SPSS) version 8.0 on a Gateway Solo laptop computer. Comparisons between treatment and control groups for motility, acrosome reaction, viability, and morphology were analyzed using the General Linear Model (GLM). Motility at any specific time point, time to zero motility, and time to last full insemination were compared between the treatment and control groups using paired t-tests. Chi-square analysis was used for comparison of the forward progression data.

Preliminary data analysis revealed there was no a dog-treatment interaction. However, the dogs could be classified into two groups based on based on the their tolerance to traditional methods. Dogs whose control samples did not have at least twenty percent motility at the zero hour evaluation and/or did not maintain at least twenty percent motility at the one hour evaluation were labeled "Intolerant" to traditional methods. All other dogs were considered to be "Tolerant" to traditional methods. Of the ten dogs represented in this study five were considered "Tolerant" and five were considered "Intolerant." General observations were made based on this tolerance or intolerance designation.

Motility

Figure 7:
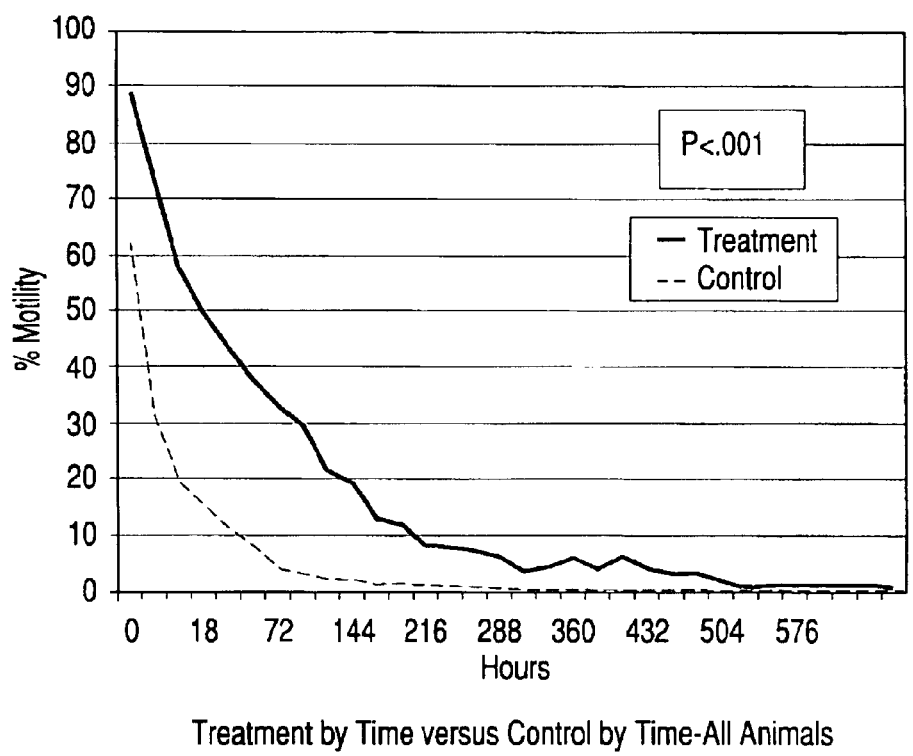
FIG. 7 is a graphical showing of treatment by time versus control by time-all animals.
Figure 8A:
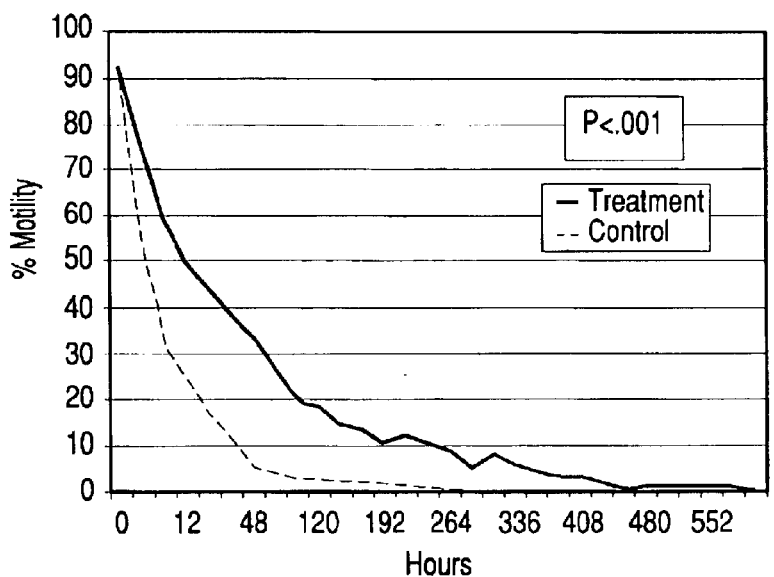
FIGS. 8a and b are graphical showings of treatment by time versus control by time for "Tolerant" and "Intolerant" animals, respectively.
Figure 8B:
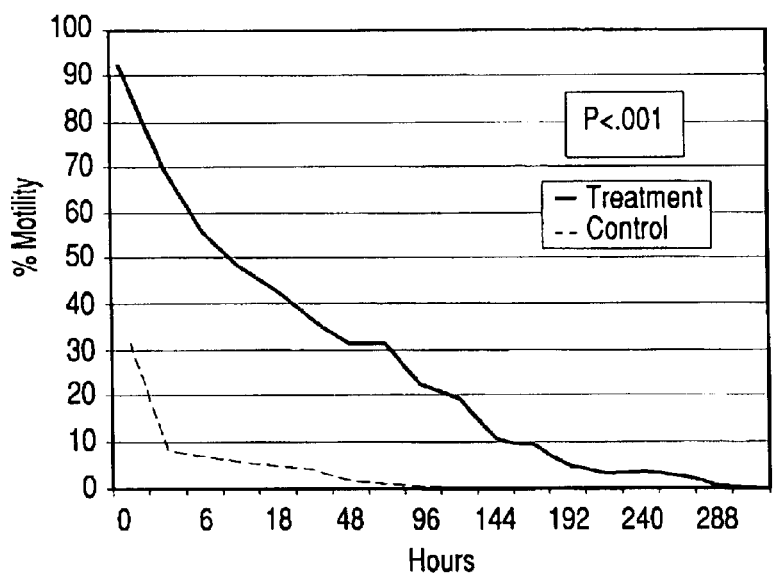

As expected, there was a difference in motility due to time (P<0.001). Also there was an overall difference between the treatment and control groups for motility (P<0.001), The difference between treatment by time versus control by time was significant (P<0.001). In addition, spermatozoa in the treatment group had significantly higher motility compared to the control at all time points past the initial evaluation up to 192 hours, where there were too few animals for an accurate analysis. The graph shown in FIG. 7 shows the difference between the treatment and control groups when all animals were included in the analysis. There was also a difference between the "Tolerant" and "Intolerant" animals (P<0.001). The graphs of FIGS. 8a and 8b show the difference between the treatment by time versus control by time for both the "Tolerant" and "Intolerant" animals.

Time to Zero Percent Motility

Figure 9:
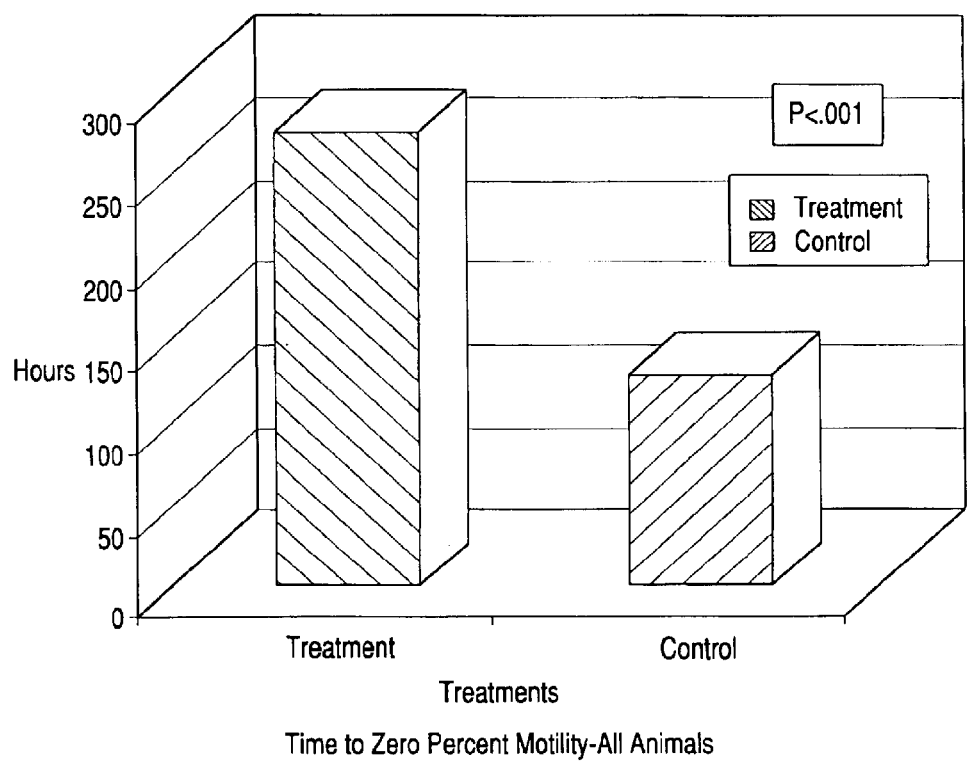
FIG. 9 is a graphical showing of time to zero percent motility-all animals.

The analysis of time to zero percent motility as seen in FIG. 9, showed a difference due to the treatment (P<0.001). The average time to zero percent motility for the control group was 129.6 hours (std. error +/−30.75) with a range of 12 to 288 hours. The average time to zero percent motility for the treatment group was 276 hours (std. error +/−49.74) with a range of 48 to 600 hours. When all dogs were included in the analysis, spermatozoa survival time increased in the treatment group an average of 378.31% over the control.

Figure 10A:
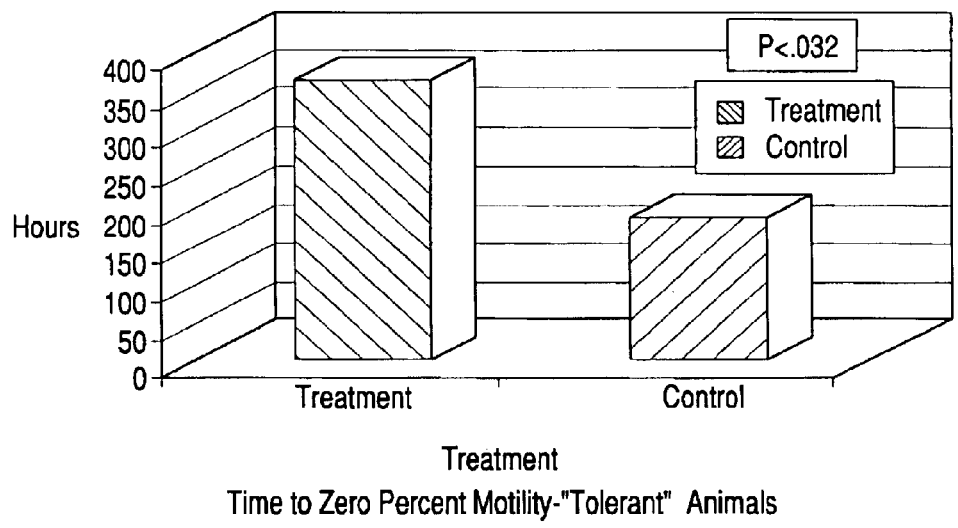
FIGS. 10a and 10b are graphical showings of time to zero percent motility for "Tolerant" and "Intolerant" animals, respectively.
Figure 10B:
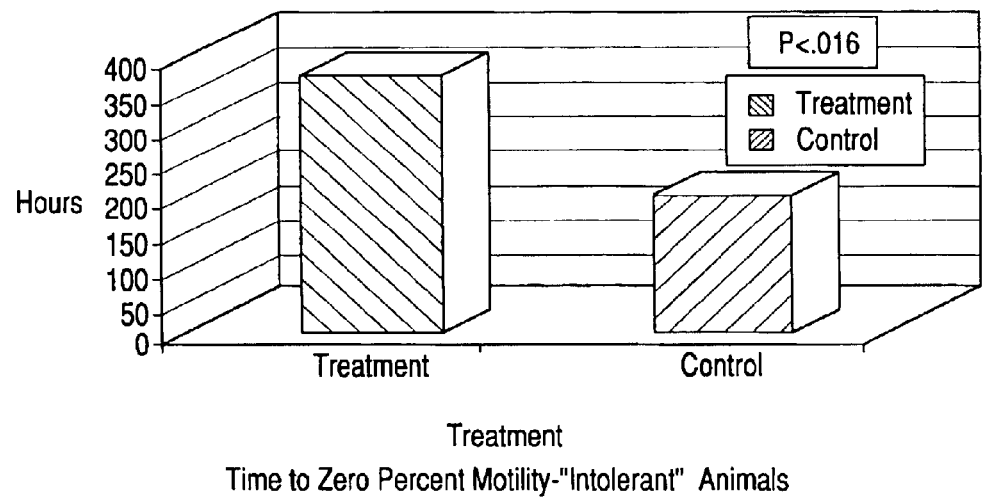

Further, the difference in the survival time of spermatozoa between the "Tolerant" and "Intolerant" animals was significant (P<0.001). Spermatozoa in the treatment group from the "Tolerant" dogs showed a 203.29% improvement in survival time over the control, while spermatozoa in the treatment group from the "Intolerant" dogs showed a 553.33% improvement in survival time over the control. Note FIGS. 10a and 10b in this context.

Time to Last Full Insemination

Figure 11:
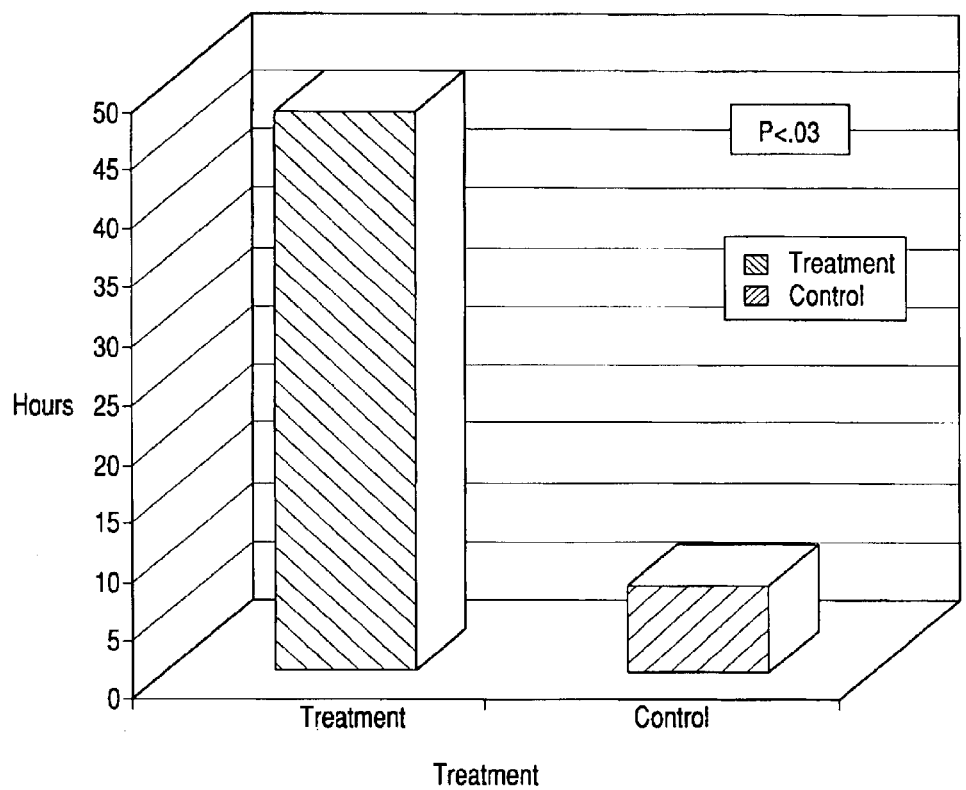
FIG. 11 is a graphical showing of time to last full insemination-animals within the 95% CI.

The analysis of time to last full insemination, as seen in FIG. 11, showed a difference due to treatment (P<0.03). The average time to last full insemination for the control group was 6.7 hours (std. error +/−2.72). The average time to last full insemination for the treatment group was 49.9 (std. error +/−18.75) The treatment group averaged 1306.67% of the control. Nine of the ten animals feel within a 95% confidence interval (CI) and maintained an average of 640.74% of the control (FIG. 5.7) A comparison of "Tolerant" and "Intolerant" groups could not be performed due to the wide variation in volume and concentration in individual animals.

Forward Progression

Figure 12:
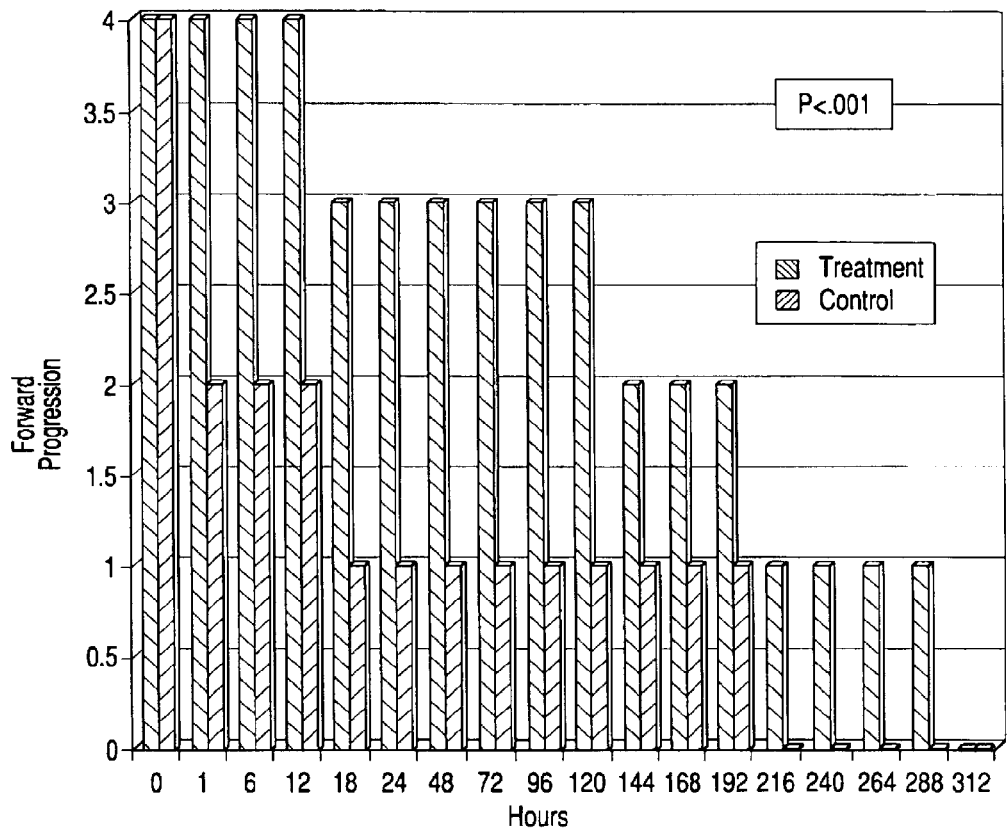
FIG. 12 is a graphical showing of forward progression-treatment by time versus control by time.

The analysis of forward progressions as depicted in FIG. 12, showed a difference between the treatment and control (P<0.001). There was also a difference between Eminent by time and control by time at time points 1 hour through 288 hours (P<0.001). The treatment group maintained a higher level of forward progression over time than the control group.

Acrosome Reaction

Figure 13:
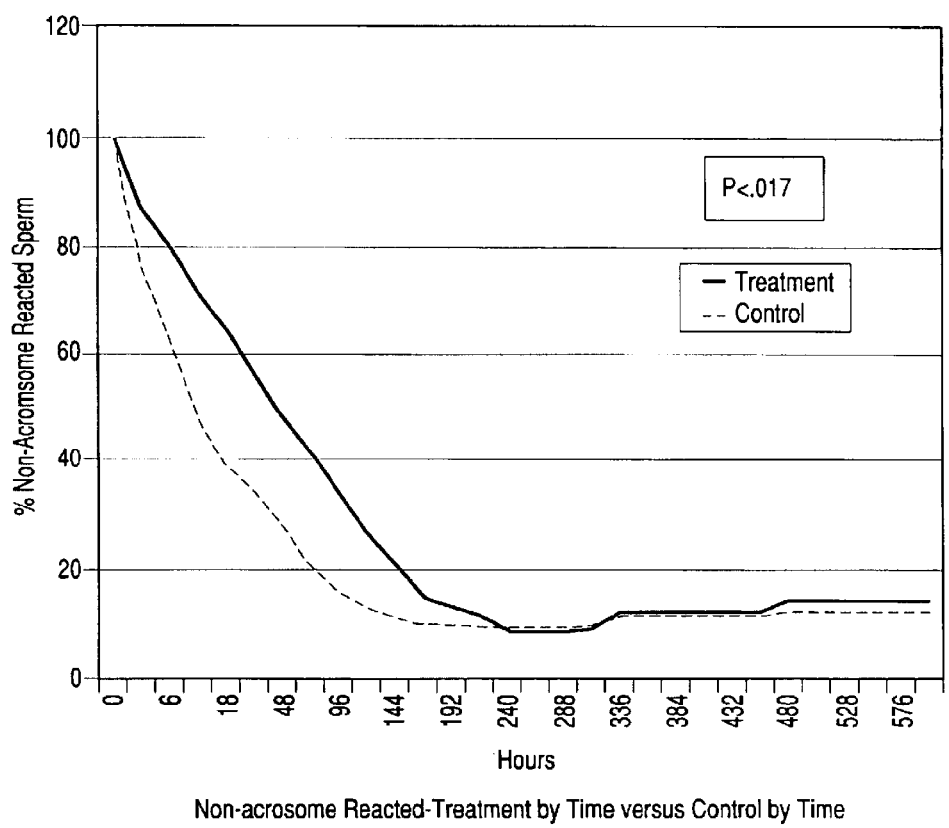
FIG. 13 is a graphical showing of non-acrosome reacted-treatment by time versus control by time.

The analysis of the percentage of the non-acrosome reacted, motile sperm, as seen in FIG. 13, showed a difference between the treatment and control groups (P<0.001). There was also a difference between the treatment by time and the control by time (P<0.017). The following chart shows the maintenance of a higher percentage of non-acrosome reacted sperm in the treatment group over time as compared to the control group over time.

Viability

Figure 14:
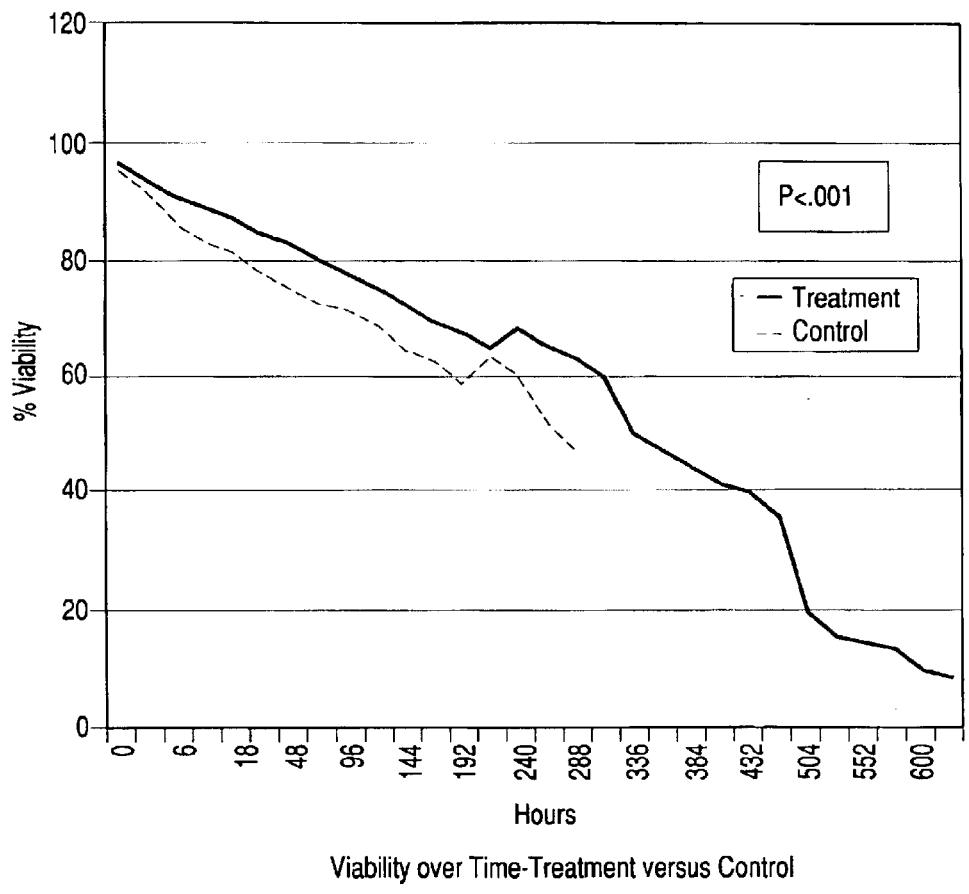
FIG. 14 is a graphical showing of viability over time-treatment versus control.

The analysis of viability, depicted in FIG. 14, showed an overall difference between the treatment and control groups (P<0.001). The following graph demonstrates the treatments increased viability over time as compared to the control group.

Morphology

Morphology for all dogs fell within the acceptable range of greater than sixty percent. There was no difference in morphology between the treatment and control groups (P<0.062), as expected. However, there was a difference in morphology over lime (P<0.001). This difference was only in tail abnormalities and was expected with the loss of motility and change associated with cell death. There was also a difference between the three investigators (P<0.002). However, each investigator found no difference between the treatment and control groups In accordance with the present invention, collection into warmed extender media lessens the cold and pH shock to the spermatozoa reported in previous studies, as shown by the improved semen parameters. This novel modification to the collection/extension of semen allows for improved preservation of spermatozoa over time when compared to traditional methods. From the data analysis, it is clear that collecting semen into warmed extender media improved the semen parameters evaluated. Specifically, the functional life span of the spermatozoa, measured as motility, was significantly increased in the treatment group as compared to the control. When comparing animals grouped as "Tolerant" and "Intolerant," both groups demonstrated improvement in motility in the treatment group. However, semen collected from those animals that were "Intolerant" to the traditional collection method appeared to demonstrate the most improvement. By collecting into the warmed extender, the temperature remained constant preventing cold shock to the spermatozoa The spermatozoa also came in contact with the buffers of the extender immediately upon collection which helped to prevent shifts in pH.

The treatment group maintained motility significantly longer than the control (time to zero motility). This held true for both the "Tolerant" and "Intolerant" groups, with the "Intolerant" samples demonstrating the greatest response to treatment. This improved motility over time led to the improvement seen in the time to last full insemination. Further, times to full acrosome reaction were delayed in the treatment group. By maintaining a greater percent of motile (and therefore viable), non-acrosome reacted sperm, the treatment group maintained a full insemination dose for a greater length of time as compared to the control. By calculating the available sperm pool (total motile sperm per ejaculate), it was possible to observe that in animals with good concentration and volume had a greater number of inseminations upon collection and maintained at least one full insemination dose much longer due to the treatment. In animals that had lower concentrations and/or volumes, it was possible to get an insemination by using the treatment where no insemination would have been available using traditional methods.

By utilizing this modification in the collection/extension method, it is possible to improve semen parameters in both the "Tolerant" and "Intolerant" animals, with the "Intolerant" animals appearing to demonstrate the most improvement. Semen from animals with a good volume and concentration can be extended and maintained for a longer period of time as compared to traditional methods, allowing for improved ability in shipping fresh-extended semen. Animals that would not have an adequate semen sample for insemination, when using traditional methods, would now have to ability to be used for AI.

What is claimed is:

1. A method for collecting semen of an animal including:

selecting a species of animal whose semen is to be collected;

determining an expected volume of semen to be collected from said selected species of animal;

providing a species specific semen collection vessel in accordance with said expected volume of semen to be collected, warming said semen collection vessel;

selecting a species-specific semen extender solution appropriate for use with said species of animal whose semen is to be collected;

warming said semen extender solution;

placing a first volume of said warmed species-specific semen extender solution in said warmed semen collection vessel, said first volume being in the range of 20% to 100% of said expected volume of semen;

receiving said semen in said semen collection vessel containing said first volume of said species-specific semen extender solution, and forming a first extended semen solution;

determining a received volume of said semen collected in said semen collection vessel;

adding additional warmed species-specific semen extender solution having a second volume to said first extended semen solution in said semen collection vessel;

selecting said second volume of said warmed species-specific semen extender solution for forming a combined volume of said received semen and said first and second semen extender solutions having a final volume such that said final volume is approximately two to three times said received volume of semen collected in said semen collection vessel; and maintaining said final volume of said collected semen and said species-specific extender solution warmed.

2. The method for collecting semen of claim 1 further including providing said animal having normal fertility.

3. The method for collecting semen of claim 1 further including providing said animal having sub-normal fertility.

4. The method of collecting semen of claim 1 further including maintaining said warmed semen collection vessel and said warmed species-specific semen extender solution at a temperature similar to a temperature of said semen to be collected upon ejaculation of said semen from an animal whose semen is to be collected.

5. The method of collecting semen of claim 4 further including placing said additional warmed species-specific semen extender solution at said temperature of said semen upon ejaculation of said semen from an animal whose semen is to be collected before adding said additional warmed species-specific semen extender solution to said first extended semen volume.

6. The method of collecting semen of claim 1 further including providing said semen collection vessel having first and second collection receptacles.

7. The method for collecting semen of claim 1 further including insulating said semen collection vessel.

8. The method of claim 1 further including providing said semen collection vessel as a cylindrical vessel.

9. The method of claim 6 further including providing said semen collection vessel including a y-tube having first and second branches.

10. The method of claim 9 including placing said semen collection vessel in fluid connection with a selected one of said branches of said y-tube.

11. The method of claim 10 further including separating said semen to be collected into a sperm-rich fraction and a sperm-poor fraction and directing said sperm-rich fraction of said semen to said semen collection vessel.

12. The method of claim 1 further including maintaining said species-specific semen extender at a pH of approximately 7.4.

* * * * *